US00PP15284P3

(12) United States Plant Patent
Beineke

(10) Patent No.: US PP15,284 P2
(45) Date of Patent: Nov. 2, 2004

(54) BLACK WALNUT TREE NAMED 'BEINEKE 3'

(50) Latin Name: *Juglans nigra L.*
Varietal Denomination: Beineke 3

(75) Inventor: Walter Beineke, West Lafayette, IN (US)

(73) Assignee: American Forestry Technologies, Inc., West Point, IN (US)

( * ) Notice: Subject to any disclaimer, the term of this patent is extended or adjusted under 35 U.S.C. 154(b) by 0 days.

(21) Appl. No.: 10/141,102

(22) Filed: May 8, 2002

(65) Prior Publication Data

US 2003/0213037 P1 Nov. 13, 2003

(51) Int. Cl.[7] ..... A01H 5/00
(52) U.S. Cl. ..... Plt./154
(58) Field of Search ..... Plt./154

(56) References Cited

U.S. PATENT DOCUMENTS

| | | | |
|---|---|---|---|
| PP4,132 | P | 10/1977 | Genn |
| PP4,388 | P | 2/1979 | Forde |
| PP4,389 | P | 2/1979 | Forde |
| PP4,405 | P | 4/1979 | Forde |
| PP4,542 | P | 6/1980 | Beineke |
| PP4,543 | P | 6/1980 | Beineke |
| PP4,614 | P | 1/1981 | Beineke |
| PP4,954 | P | 11/1982 | Beineke |
| PP4,955 | P | 11/1982 | Beineke |
| PP4,964 | P | 12/1982 | Beineke |
| PP4,966 | P | 12/1982 | Beineke |
| PP4,968 | P | 12/1982 | Beineke |
| PP4,971 | P | 1/1983 | Beineke |
| PP6,973 | P | 8/1989 | Madison |
| PP9,906 | P | 6/1997 | Jones |
| PP9,924 | P | 6/1997 | Jones |
| PP9,925 | P | 6/1997 | Jones |

OTHER PUBLICATIONS

Appleton, Bonnie, et al. (2000) "Trees for problem Landscape Sites—The Walnut Tree: Allelopathic Effects and Tolerant Plants" *Virginia State University* Publication No. 430–021.
Beineke, Walter F. (1989) "Twenty Years of Black Walnut Genetic Improvement at Purdue University" *NJAF* 6:68–71.
Coladonato, Milo (1991) "*Juglans Nigra*" 1–11.
Esser, Lora. (1993) "*Juglans Californica*" 1–11.
Pavek, Diane S. (1993) "*Juglans Major*" 1–13.
Tirmenstein, D.S (1990) "*Juglans Microcarpa*" 1–11.
Website: http://www.treeguide.com/naspecies.asp?treeid=junigr1: printed Aug. 30, 2001: pp. 1–11.
Website: http://virual.clemson.edu/groups/FieldOps/Cgs/walnut.htm: printed Aug. 30, 2001: pp. 1–3.
Woeste, K., et al. (2002) "Thirty Polymorphic Nuclear Microsatellite Loci From Black Walnut" *The Journal of Heredity* 93(1):58–60.

*Primary Examiner*—Kent Bell
(74) *Attorney, Agent, or Firm*—Alice O. Martin; Barnes & Thornburg

(57) ABSTRACT

A new and distinct cultivar of black walnut tree (*Juglans nigra L.*) which is distinctly characterized by extremely rapid growth rate, very strong central stem tendency, and excellent straightness, thereby producing excellent timber qualities. This new variety of black walnut tree (*Juglans nigra L.*) was discovered by the applicant near West Lafayette, Ind. in a black walnut planting of seedling progeny from a previously selected tree for outstanding timber producing potential. This selection has been designated as BW426, a seedling progeny of selection number BW95 in records maintained by the applicant on the performance of the selection and grafts made from the selection and will be known henceforth as 'Beineke 3'.

3 Drawing Sheets

Latin name of the genus and species: *Juglans nigra L.*

BACKGROUND OF THE INVENTION

This new variety of black walnut tree (*Juglans nigra L.*) was discovered by the applicant near West Lafayette, Ind. in a black walnut planting of seedling progeny from previously selected trees for outstanding timber producing potential (Beineke, 1989). This selection has been designated as BW426, a seedling progeny of selection number BW95 (unpatented) in records maintained by the applicant on the performance of the selection and grafts made from the selection and will be known henceforth as 'Beineke 3'. The male parent is unknown, as is generally the case with black walnut trees (Beineke, 1989).

SUMMARY OF THE INVENTION

A new and distinct cultivar of black walnut tree (*Juglans nigra L.*) is distinctly characterized by extremely rapid growth rate, very strong central stem tendency, and excellent straightness, thereby producing excellent timber qualities. Beineke 3 was 17 years old when described at a location near West Lafayette, Ind.

After the original clone was selected, and assigned an identity number of BW426 the aforesaid tree was reproduced by collecting scions from it and grafting these onto common black walnut rootstocks at American Forestry Technology Company, West Point, Ind. These asexual reproductions ran true to the originally discovered tree and to each other in all respects.

Color values used were from the Munsell Color Chart for Plant Tissues. However, color is too dependent on weather conditions and fertilization to be consistent or distinctive. For example, leaves can be made a deeper green by applying nitrogen. Walnut tree leaves turn yellow as the season progresses, especially if there is a lack of rainfall. As black walnut meats dry, they become darker. Simply being on the ground for a week causes the outer shell to darken. Bark color involves many shades of gray through brown and black.

Beineke 3 is hardy in USDA zones 4, 5, 6, 7, and 8.

BOTANICAL DESCRIPTION OF THE PLANT

Figure 1:
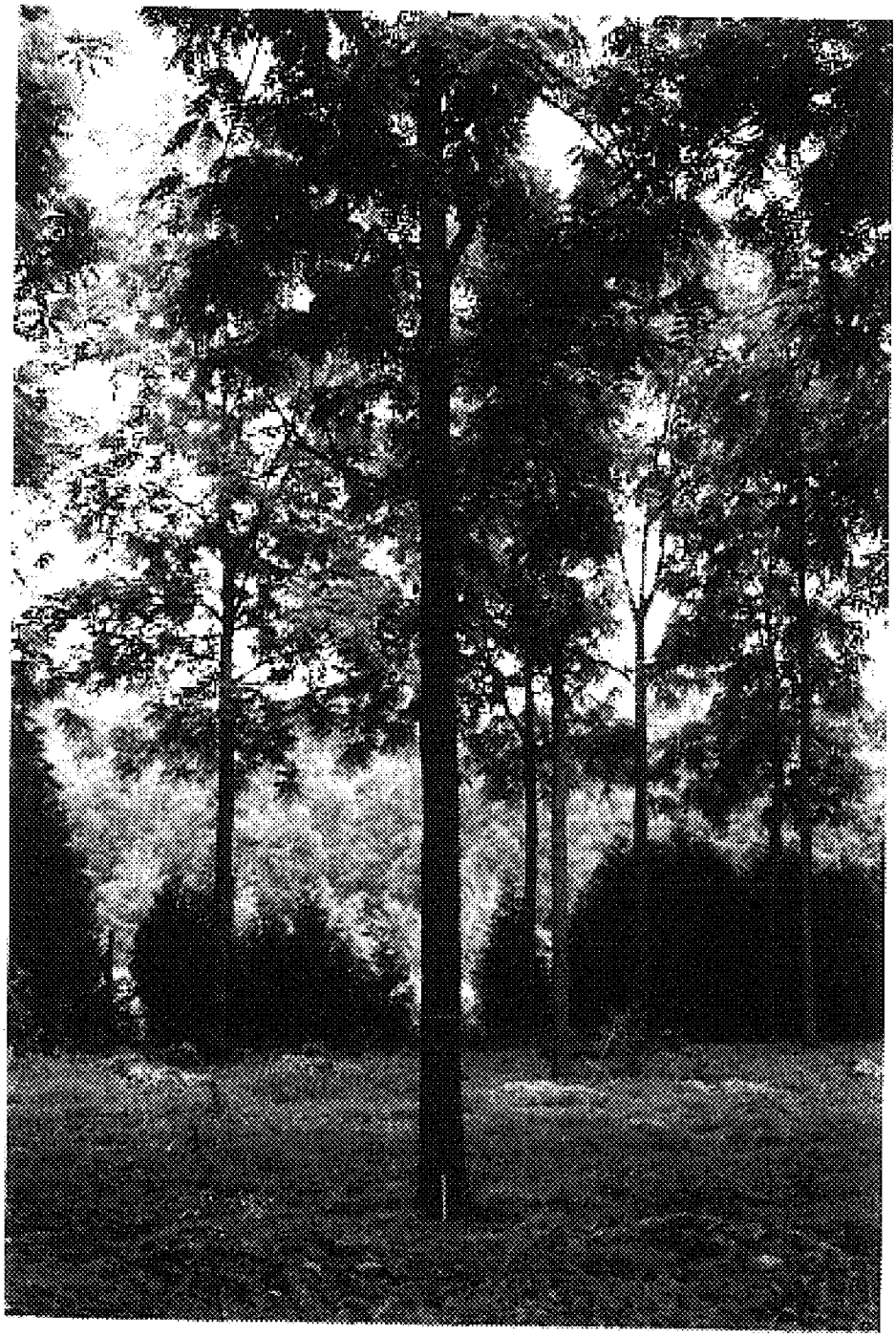
FIG. 1 is a photograph showing the timber form of 'Beineke 3.'
Figure 2:
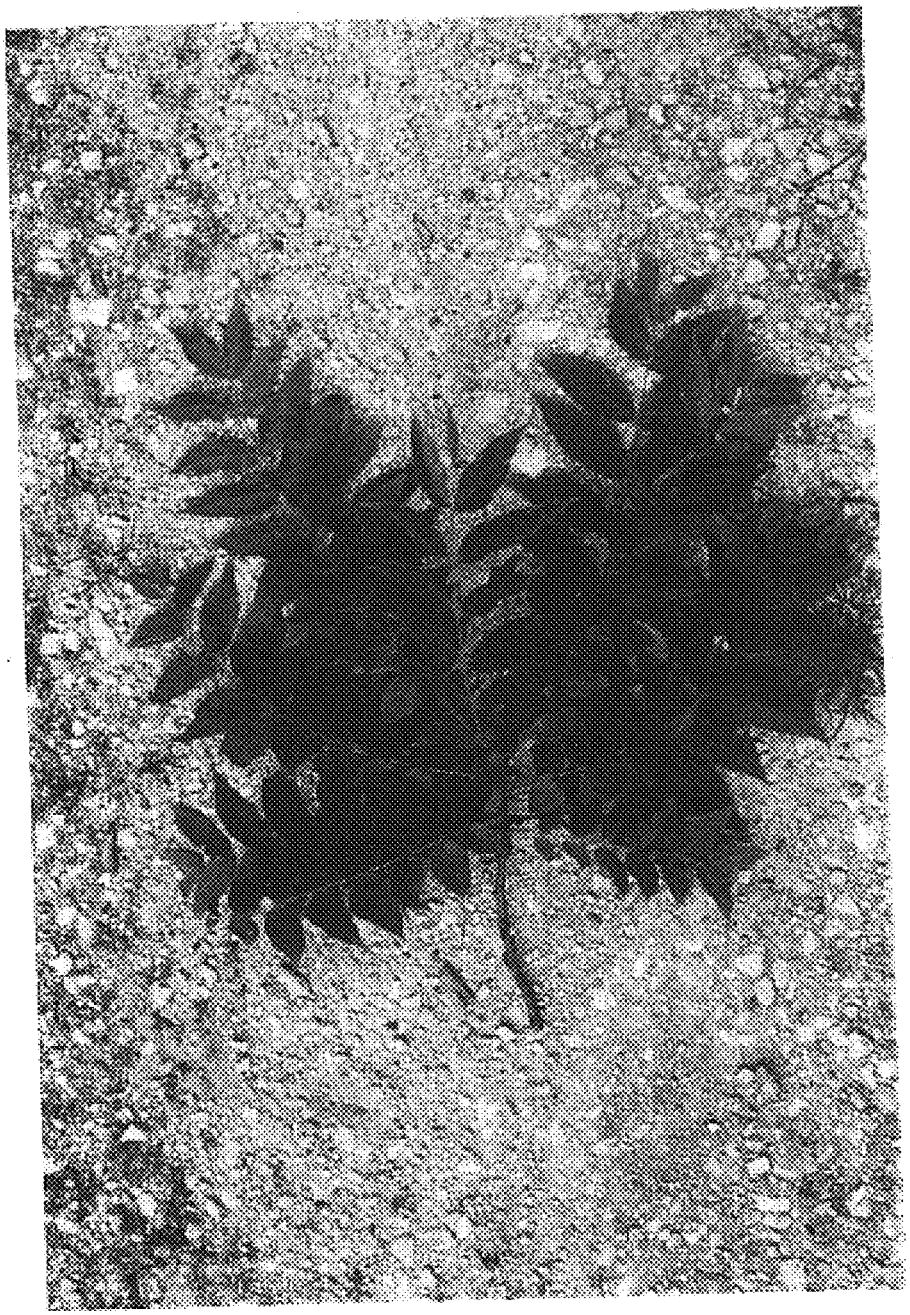
FIG. 2 is a photograph showing the leaves of 'Beineke 3.'

The botanical details of this new and distinct variety of walnut tree are as follows:

Tree:

*Size.*—Large, 54 ft.; at 17 years old crown diameter of 15 ft.

*Vigor.*—Vigorous.

*Growth rate.*—Very rapid, faster than Purdue 1 (U.S. Plant Pat. No. 4,543) and Tippecanoe 1 (U.S. Plant Pat. No. 4,954) — 36% and 8% larger in diameter than the average of Purdue 1 and Tippecanoe 1 grafts respectively, planted the same year on the same land. Diameter growth rate (at 4½ feet above the ground) averages 0.588 inches per year, over 17 years about 10 inches.

*Form.*—Excellent timber form, stem better than Purdue 1 (U.S. Plant Pat. No. 4,543) and Tippecanoe 1 (U.S. Plant Pat. No. 4,954) — 36% straighter than average of the entire planting. On a rating scale of 1 (excellent) to 5 (very poor), Beineke 3 averages 1 no crooks, very strong central stem tendency. Stem form was obtained by subjectively rating the straightness of the main stem on a scale of 1 to 5 with 1 representing a perfectly straight stem; 2, slight crook or deviation of the central stem; 3, about average straightness; 4, several severe crooks or a single fork; and 5, a very crooked, forked and/or leaning central stem. The original tree was cut and no parental trees were planted on the same site. However, Beineke 3 was straighter than BW95.

The trees of the present invention are grown in plantations, not open fields (not natural stands). In plantations, trees are upright and have no distinctive or characteristic crown shape because all branches are seeking to grow upwards.

Branches: Diameter depends on age and size of tree, varies from ½" to 12", bark color varies from grays to browns.

Leaves:

*Compound leaves.*—Size — Much shorter than average; average length — 13.7 inches.

*Leaflets.*—Size — Average; average length — 3.9 inches; Width about 3.0 inches; average number of leaflets — 16.9 — lanceolate; acutely pointed. Thickness — thin; Texture — smooth; Margin — serrated; Color — Topside — dark green; (2.5G4/4 by the Munsell Color Chart for Plant Tissues). Underside — light green (5GY5/4 on the Munsell Color Chart for Plant Tissues).

*Anthracnose resistance.*—Excellent.

*Petioles.*—short.

Flowering habit:

*Age at which trees start producing catkins.*—Early, it takes about 4–5 years to flower.

*Number of catkins produced.*—Abundant.

*Size of catkins.*—Very long.

*Time of pollen shed.*—Early.

*Age at which tree starts producing pistillate flowers.*—Early.

*Number of pistillate flowers produced by young trees.*—Abundant.

*Number of pistillate flowers produced by mature trees.*—Abundant.

*Lateral shoots producing pistillate flowers.*—None.

*Number of pistillate flowers per inflorescence.*—2 and 3.

*Flowering season.*—Generally May in Indiana.

Flower season: Flowers typically in May in Indiana. There are probably 1-million pollen per catkin. Female flowers are about 1/16" long and grow to two "pollen pick up points" which subsequently break apart. Pollen exits as "dust" which is not feasible to quantitate.

Nut crop:

*Bearing.*—Biennial, early October but only every other year.

*Productivity.*—Heavy.

*Ripening period.*—Late.

*Evenness of maturity (period between first and last nuts are ready for harvest).*—Even.

*Quality.*—Good.

*Distribution of nuts on tree.*—Throughout.

*Color.*—Mottled, 5YR and 2.5YR3/4 by the Munsell Color Chart for Plant Tissue.

Nut:

*Size.*—Small; average length — 1.3"; average diameter in suture plane — 1.0"; average diameter cheek to cheek — 1.3".

*Uniformity of size.*—Not much variation.

Figure 3:
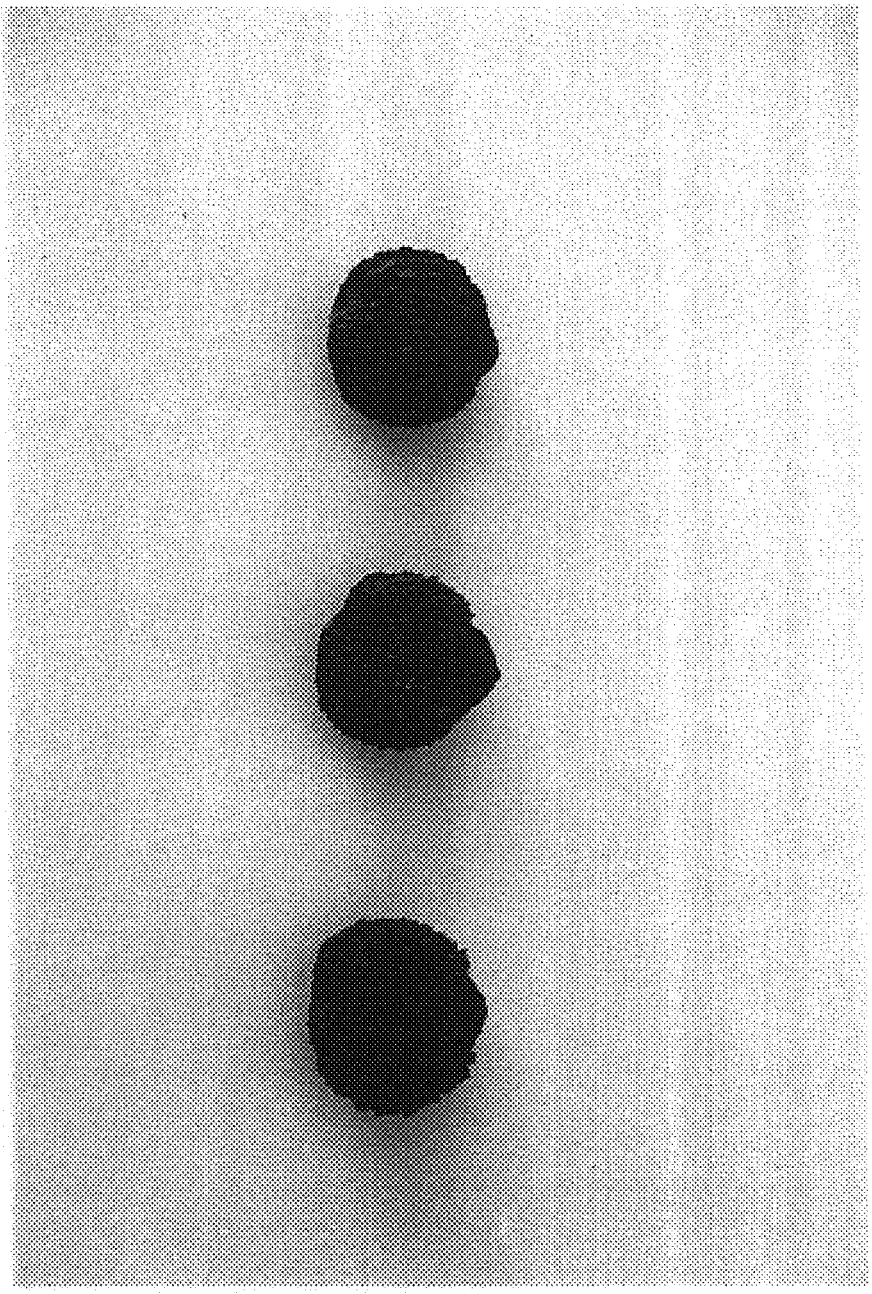
FIG. 3 is a photograph showing the nuts of 'Beineke 3.'

*Form.*—Round; Somewhat flattened in suture plane. See FIG. 3.

*Blossom end.*—Flattened.

*Basal end.*—Rounded to obtusely pointed.

*Thickness of shell.*—Very thick.

*Ridges.*—Sharp ridges.

GENETIC METHOD OF IDENTIFICATION

DNA "fingerprint" for identification of 'Beinke 3'.

DNA was isolated from the leaves of 'Beineke 3.' For purposes of DNA fingerprinting, nine highly polymorphic loci from a suite of microsatellites developed by Woeste et al. (2002) were chosen. Microsatellites sizes were checked against previously published standards and verified by a second independent analysis. The "fingerprint" is the collection of microsatellite allele sizes at each locus for 'Beineke 3.'

DNA was isolated from the leaves of 10 black walnut trees obtained from Walter Beineke using CTAB extraction buffer (50 mM TRIS-HCL, pH 8.0, 20 mM EDTA, pH 8.0, 0.7 M NaCl, 0.4 M LiCl, 2% SDS, 2% TAB, nd 1% PVP). After isolation the DNA from each tree was quantified and diluted with nanopure distilled water to a final concentration of 5 ng/$\mu$L. The samples were stored in 96-well plates at 20° C.

For purposes of DNA fingerprinting, nine highly polymorphic loci from a suite of microsatellites developed by Woeste et al. (2002) were chosen. Amplification of each locus was performed with an MJ Research Tetrad Thermocycler (Waltham, Mass.) using 10 μL reactions in 96-well plates. The PCR reaction mix contained 2 μL of the aforementioned black walnut DNA, 5 μL Sigma Taq ReadyMix (Sigma Aldrich, St. Louis, Mo.), 0.4 μL of a 20 pmol mixture of forward and reverse fluorescence labeled primer, and 3 μL PCR grade water supplied with the Sigma ReadyMix. PCR amplification was for 30 cycles of 94° C. for 20 sec, 55° C. for 30 sec, and 72° C. for 1 min. All primers were annealed at 55° C. The products were then held at 4° C. until aliquots could be loaded into 6% Long Ranger (polyacrylamide) denaturing gels (BMA, Rockland, Me.). For each individual 0.5 μL PCR product was added to 0.75 μL blue dextran and 0.25 μL of CXR 350 bp Ladder Standard (Promega, Fitchburg Center, Wis.) in a new 96-well 1 late. The samples were denatured for 2 min at 95° C. and loaded onto a CAL96 96-well laminated membrane comb (The Gel Company, San Francisco, Calif.). Electrophoresis was at 3,000 V, 60 mA, 200 Watts, 50° C. for 2 hours using an ABI 377 (Perkin Elmer) with 36 cm plates and 0.2 mm spacers. The resulting data was analyzed using ABI's GeneScan 3.1.2 and Genotyper 2.5 (Perkin Elmer). Microsatellite sizes were checked against previously published standards and verified by a second independent analysis. The "fingerprint" is the collection of microsatellite allele sizes at each locus for each tree.

| Locus | Forward | Reverse |
|---|---|---|
| WGA2 | GACGACGAAGGTGTACGGAT (SEQ ID NO: 1) | GTACGGCTCTCCTTGCAGTC (SEQ ID NO: 10) |
| WGA6 | CCATGAAACTTCATGCGTTG (SEQ ID NO: 2) | CATCCCAAGCGAAGGTTG (SEQ ID NO: 11) |
| WGA24 | TCCCCCTGAAATCTTCTCCT (SEQ ID NO: 3) | TTCTCGTGGTGCTTGTTGAG (SEQ ID NO: 12) |
| WGA32 | CTCGGTAAGCCACACCAATT (SEQ ID NO: 4) | ACGGGCAGTGTATGCATGTA (SEQ ID NO: 13) |
| WG33 | TGGTCTGCGAAGACACTGTC (SEQ ID NO: 5) | GGTTCGTCGTTTGTTGACCT (SEQ ID NO: 14) |
| WGA86 | ATGCCTCATCTCCATTCTGG (SEQ ID NO: 6) | TGAGTGGCAATCACAAGGAA (SEQ ID NO: 15) |

-continued

| Locus | Forward | Reverse |
|---|---|---|
| WGA89 | ACCCATCTTTCACGTGTGTG (SEQ ID NO: 7) | TGCCTAATTAGCAATTTCCA (SEQ ID NO: 16) |
| WGA90 | CTTGTAATCGCCCTCTGCTC (SEQ ID NO: 8) | TACCTGCAACCCGTTACACA (SEQ ID NO: 17) |
| WGA97 | GGAGAGGAAAGGAATCCAAA (SEQ ID NO: 9) | TTGAACAAAAGGCCGTTTTC (SEQ ID NO: 18) |

The best interpretation of the current data indicates that the probability that any other black walnut tree would have the collection of microsatellite allele sizes listed is less that 1 in $10^{-17}$.

Sizes (bp) of microsatelites at 9 loci used to fingerprint 'Beineke 3' (2 alleles at each locus)

| WGA2 | | WGA6 | | WGA24 | | WGA32 | | WGA90 | |
|---|---|---|---|---|---|---|---|---|---|
| 150 | 150 | 142 | 158 | 230 | 236 | 189 | 191 | 140 | 154 |
| WGA86 | | WGA97 | | WGA33 | | WGA89 | | | |
| 226 | 238 | 157 | 161 | 220 | 220 | 191 | 197 | | |

DOCUMENTS CITED

Beineke, Walter F. (1989) Twenty years of black walnut genetic improvement at Purdue University *North. J. Appl. For.* 6:68–71.

Woeste, K., Burns, R., Rhodes, O., and Michler, C. (2002) (In Press) Thirty polymorphic nuclear microsatellite loci from black walnut. *Journal of Heredity.*

I claim:

1. A new and distinct variety of black walnut tree named 'Beineke 3' substantially as illustrated and described, which has excellent timber quality, is fast growing, has strong central stem tendency, no sweep, and no crooks.

* * * * *

UNITED STATES PATENT AND TRADEMARK OFFICE

CERTIFICATE OF CORRECTION

PATENT NO. : PP 15,284 P2
APPLICATION NO. : 10/141102
DATED : November 2, 2004
INVENTOR(S) : Walter F. Beineke It is certified that error appears in the above-identified patent and that said Letters Patent is hereby corrected as shown below:

In Column 6, line 38, after "Journal of Heredity" add "93(1):58-60".
Below "Sequence Listing" should be inserted between the end of "Documents Cited" and "I Claim"

SEQUENCE LISTING
<110> BEINEKE, WALTER F.
<120> BLACK WALNUT TREE NAMED "BEINEKE 3"
<130> 30034-92644
<140> 10/141,102
<141> 2002-05-08
<160> 18
<170> PatentIn Ver. 2.1

<210> 1
<211> 20
<212> DNA
<213> Artificial Sequence

<220>
<223> Description of Artificial Sequence: Primer

<400> 1
gacgacgaag gtgtacggat 20

<210> 2
<211> 20
<212> DNA
<213> Artificial Sequence

<220>
<223> Description of Artificial Sequence: Primer

<400> 2
ccatgaaact tcatgcgttg 20

<210> 3
<211> 20
<212> DNA
<213> Artificial Sequence

UNITED STATES PATENT AND TRADEMARK OFFICE

CERTIFICATE OF CORRECTION

PATENT NO. : PP 15,284 P2
APPLICATION NO. : 10/141102
DATED : November 2, 2004
INVENTOR(S) : Walter F. Beineke It is certified that error appears in the above-identified patent and that said Letters Patent is hereby corrected as shown below:

<220>
<223> Description of Artifical Sequence: Primer

<400> 3
tccccctgaa atcttctcct 20

<210> 4
<211> 20
<212> DNA
<213> Artificial Sequence
<220>
<223> Description of Artificial Sequence: Primer <400> 4
ctcggtaagc cacaccaatt 20

<210> 5
<211> 20
<212> DNA
<213> Artificial Sequence

<220>
<223> Description of Artificial Sequence: Primer

<400> 5
tggtctgcga agacactgtc 20

<210> 6
<211> 20
<212> DNA
<213> Artificial Sequence

<220>
<223> Description of Artificial Sequence: Primer

<400> 6
atgcctcatc tccattctgg 20

UNITED STATES PATENT AND TRADEMARK OFFICE

CERTIFICATE OF CORRECTION

PATENT NO. : PP 15,284 P2
APPLICATION NO. : 10/141102
DATED : November 2, 2004
INVENTOR(S) : Walter F. Beineke It is certified that error appears in the above-identified patent and that said Letters Patent is hereby corrected as shown below:

<210> 7
<211> 20

<212> DNA
<213> Artificial Sequence

<220>
<223> Description of Artificial Sequence: Primer

<400> 7
acccatcttt cacgtgtgtg 20

<210> 8
<211> 20
<212> DNA
<213> Artificial Sequence

<220>
<223> Description of Artificial Sequence: Primer

<400> 8
cttgtaatcg ccctctgctc 20

<210> 9
<211> 20
<212> DNA
<213> Artificial Sequence

<220>
<223> Description of Artificial Sequence: Primer

<400> 9
ggagaggaaa ggaatccaaa 20

<210> 10
<211> 20
<212> DNA
<213> Artificial Sequence

<220>

It is certified that error appears in the above-identified patent and that said Letters Patent is hereby corrected as shown below:

<223> Description of Artificial Sequence: Primer

<400> 10
gtacggctct ccttgcagtc 20

<210> 11
<211> 18
<212> DNA
<213> Artificial equence

<220>
<223> Description of Artificial Sequence: Primer

<400> 11
catcccaagc gaaggttg 18

<210> 12
<211> 20
<212> DNA
<213> Artificial Sequence

<220>
<223> Description of Artificial Sequence: Primer

<400> 12
ttctcgtggt gcttgttgag 20

<210> 13
<211> 20 <212> DNA
<213> Artificial Sequence

<220>
<223> Description of Artificial Sequence: Primer

<400> 13
acgggcagtg tatgcatgta 20

<210> 14
<211> 20

It is certified that error appears in the above-identified patent and that said Letters Patent is hereby corrected as shown below:

<212> DNA
<213> Artificial Sequence

<220>
<223> Description of Artificial Sequence: Primer

<400> 14
ggttcgtcgt ttgttgacct 20

<210> 15
<211> 20
<212> DNA
<213> Artificial Sequence

<220>
<223> Description of Artificial Sequence: Primer

<400> 15
tgagtggcaa tcacaaggaa 20

<210> 16
<211> 20
<212> DNA
<213> Artificial Sequence

<220>
<223> Description of Artificial Sequence: Primer

<400> 16
tgcctaatta gcaatttcca 20

<210> 17
<211> 20
<212> DNA
<213> Artificial Sequence
<220>
<223> Description of Artificial Sequence: Primer

<400> 17

UNITED STATES PATENT AND TRADEMARK OFFICE

CERTIFICATE OF CORRECTION

PATENT NO. : PP 15,284 P2
APPLICATION NO. : 10/141102
DATED : November 2, 2004
INVENTOR(S) : Walter F. Beineke It is certified that error appears in the above-identified patent and that said Letters Patent is hereby corrected as shown below:

tacctgcaac ccgttacaca 20

<210> 18
<211> 20
<212> DNA
<213> Artificial Sequence

<220>
<223> Description of Artificial Sequence: Primer

<400> 18
ttgaacaaaa ggccgttttc 20

Signed and Sealed this

Fifth Day of September, 2006

JON W. DUDAS
*Director of the United States Patent and Trademark Office*